(12) United States Patent
Guan et al.

(10) Patent No.: US 6,407,188 B1
(45) Date of Patent: Jun. 18, 2002

(54) POLYMERIZATION OF OLEFINS

(75) Inventors: Zhibin Guan, Irvine, CA (US); Lin Wang, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 33 days.

(21) Appl. No.: 09/672,613

(22) Filed: Sep. 28, 2000

Related U.S. Application Data

(60) Provisional application No. 60/156,681, filed on Sep. 29, 1999.

(51) Int. Cl.[7] ............................... C08F 2/34; C08F 4/70; C08F 4/80

(52) U.S. Cl. ........................ 526/113; 526/115; 526/117; 526/118; 526/119; 526/161; 526/169.1; 526/172

(58) Field of Search ................................. 526/113, 115, 526/117, 118, 119

(56) References Cited

U.S. PATENT DOCUMENTS

| | | |
|---|---|---|
| 5,071,927 A | 12/1991 | Benham et al. |
| 5,137,994 A | 8/1992 | Goode et al. |
| 5,686,542 A | 11/1997 | Ostoja-Starzewski et al. |
| 5,753,785 A | 5/1998 | Reddy et al. |
| 5,856,610 A | 1/1999 | Tamura et al. |
| 6,214,761 B1 * | 4/2001 | Bennett ...................... 502/117 |
| 6,262,196 B1 * | 7/2001 | Mecking ..................... 526/114 |

FOREIGN PATENT DOCUMENTS

| | | |
|---|---|---|
| WO | WO 90/15085 | 12/1990 |
| WO | WO 97/48735 | 12/1997 |
| WO | WO 98/38228 | * 9/1998 |
| WO | WO 99/50318 | 10/1999 |

OTHER PUBLICATIONS

Denger et al., *Simultaneous oligomerization and polymerization of ethylene*, Makromol. Chem., Rapid Commun., 1991, p. 697–701, vol. 12.

Benham, E. A. et al., *A Process for the Simultaneous Oligomerization and Copolymerization of Ethylene*, Polymer Engeineering and Science, 1988, p. 1469 01472, vol. 28, No. 22.

Mecking, S., Reactor blending with early/late transition metal catalyst combinations in ethylene polymerization, Macromol. Rapid Commun., 1999, p. 139–143, vol. 20, No. 3.

International Search Report PCT/US00/26644 dated 09/28/00.

* cited by examiner

*Primary Examiner*—David W. Wu
*Assistant Examiner*—R. Rabago

(57) ABSTRACT

A branched polyolefin, preferably a polyethylene, and containing branches with even and odd numbers of carbon atoms, may be made by oligomerizing ethylene to an α-olefin using a selected iron containing catalyst, and then copolymerizing that α-olefin with ethylene and one or more other added α-olefins which have odd numbers of carbon atoms. The polymers are useful, for example, as molding resins.

13 Claims, No Drawings

POLYMERIZATION OF OLEFINS

CROSS-REFERENCE TO RELATED APPLICATION

This application claims priority under 35 U.S.C. §119 from U.S. Provisional Application Ser. No. 60/156,681 (filed Sep. 29, 1999), which is incorporated by reference herein as if fully set forth.

FIELD OF THE INVENTION

Polymers with varied and useful properties may be produced in processes using at least one polymerization catalyst, and at least one oligomerization catalyst for ethylene which is a selected iron catalyst.

TECHNICAL BACKGROUND

Polyolefins are most often prepared by polymerization processes in which a transition metal containing catalyst system is used. Oftentimes, these transition metal catalysts will copolymerize two olefins such as ethylene and an α-olefin, especially a higher α-olefin. Such copolymers have been found very useful in a large number of fields; however, the higher cost of the α-olefin is a negative for these types of polymers compared to polymers made only from cheap olefins such as ethylene or propylene.

Various reports of "simultaneous" oligomerization and polymerization of ethylene to form (in most cases) branched polyethylenes have appeared in the literature, see for instance WO90/15085, WO 99/50318, U.S. Pat. Nos. 5,753,785, 5,856,610, 5,686,542, 5,137,994 and 5,071,927; C. Denger, et al, *Makro-mol. Chem. Rapid Commun.*, vol. 12, p. 697–701 (1991); and E. A. Benham, et al., *Polymer Engineering and Science*, vol. 28, p. 1469–1472 (1988). None of these references specifically describes any of the processes or resulting branched polyolefins herein.

SUMMARY OF THE INVENTION

This invention concerns a process for preparing a branched polyolefin, comprising the steps of:

(1) contacting an ethylene oligomerization catalyst and a first monomer component comprising ethylene, under conditions to oligomerize at least a portion of the ethylene to one or more even α-olefins of the general formula $R^{28}CH{=}CH_2$ wherein $R^{28}$ is alkyl containing an even number of carbon atoms, wherein the ethylene oligomerization catalyst comprises an active Fe complex of a ligand of the formula (I):

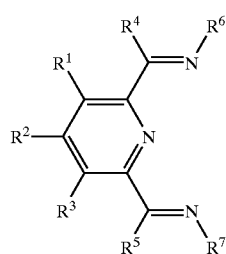

(I)

wherein:

$R^1$, $R^2$, $R^3$, $R^4$ and $R^5$ are each independently hydrogen, hydrocarbyl, substituted hydrocarbyl, or an inert functional group, provided that any two of $R^1$, $R^2$ and $R^3$ vicinal to one another, taken together may form a ring; and $R^6$ and $R^7$ are aryl or substituted aryl; and (2) contacting an active transition metal copolymerization catalyst, with a second monomer component comprising ethylene, at least a portion of the α-olefin from step (1) and an odd α-olefin of the formula $R^{18}CH{=}CH_2$ wherein $R^{18}$ is alkyl containing an odd number of carbon atoms, under conditions to copolymerize the ethylene, even α-olefin and odd α-olefin to a branched polyolefin.

The two steps of the above-mentioned process may occur separately, sequentially and/or simultaneously, as described in further detail below.

DETAILED DESCRIPTION OF THE PREFERRED EMBODIMENTS

Herein certain terms are used which are defined below.

By "hydrocarbyl" is meant a univalent radical containing only carbon and hydrogen. As examples of hydrocarbyls may be mentioned unsubstituted alkyls, cycloalkyls and aryls. If not otherwise stated, it is preferred that the hydrocarbyl groups herein contain 1 to 30 carbon atoms, and more preferably 1 to 20 carbon atoms.

By "substituted hydrocarbyl" herein is meant a hydrocarbyl group that contains one or more "inert functional groups" that are inert under the process conditions to which the compound containing these groups is subjected. The inert functional groups also do not substantially interfere with the oligomerization/polymerization process. For example, in cases in which the inert functional group may be near the complexed iron atom, such as $R^4$ or $R^5$ in (I), or as a substituent on $R^4$, $R^5$, $R^6$ or $R^7$, the inert functional group should not coordinate to the iron atom more strongly than the three depicted N groups in (I) which are the desired coordinating groups—that is, the functional group should not displace one or more of the desired coordinating N groups. The hydrocarbyl may be completely substituted, as in trifluoromethyl. If not otherwise stated, it is preferred that substituted hydrocarbyl groups herein contain 1 to about 30 carbon atoms. Included in the meaning of "substituted" are heterocyclic rings.

Examples of inert functional groups include halo (fluoro, chloro, bromo and iodo), ester, keto (oxo), amino, imino, carboxyl, phosphite, phosphonite, phosphine, phosphinite, thioether, amide, nitrile, and ether. Preferred inert functional groups are halo, ester, amino, imino, carboxyl, phosphite, phosphonite, phosphine, phosphinite, thioether, and amide. Which inert functional groups are useful in which oligomerizations/polymerizations may in some cases be determined by reference to U.S. Pat. Nos. 5,955,555, 6,103,946 and WO98/30612, all of which are hereby incorporated by reference for all purposes as if fully set forth.

By an oligomerization or polymerization "catalyst activator" is meant a compound that reacts with a transition metal compound to form an activated catalyst species. A preferred catalyst activator is an alkylaluminum compound, that is, a compound which has at least one alkyl group bound to an aluminum atom.

By "relatively noncoordinating" (or "weakly coordinating") anions are meant those anions as are generally referred to in the art in this manner, and the coordinating ability of such anions is known and has been discussed in the literature. See, for instance, W. Beck et al., *Chem. Rev.*, vol. 88, pp. 1405–1421 (1988), and S. H. Strauss, *Chem. Rev.*, vol. 93, pp. 927–942 (1993), both of which are hereby included by reference. Among such anions are those formed from aluminum compounds (such as those described in the immediately preceding paragraph) and X⁻ (an anion as discussed in further detail below), including $(R^{19})_3AlX^-$, $(R^{19})_2AlClX^-$, $R^{19}AlCl_2X^-$, and $R^{19}AlOX^-$, wherein $R^{19}$ is alkyl. Other useful noncoordinating anions include BAF⁻ {BAF=tetrakis[3,5-bis(trifluoromethyl)phenyl]borate}, $SbF_6^-$, $PF_6^-$, and $BF_4^-$, trifluoromethanesulfonate, p-toluenesulfonate, $(R_fSO_2)_2N^-$, and $(C_6F_6)_4B^-$.

By a "primary carbon group" herein is meant a group of the formula —CH₂——, wherein the free valence ——— is to any other atom, and the bond represented by the solid line is to a ring atom of an aryl or substituted aryl to which the primary carbon group is attached. Thus the free valence ——— may be bonded to a hydrogen atom, a halogen atom, a carbon atom, an oxygen atom, a sulfur atom, etc. In other words, the free valence ——— may be to hydrogen, hydrocarbyl, substituted hydrocarbyl or a functional group. Examples of primary carbon groups include —CH₃, —CH₂CH(CH₃)₂, —CH₂Cl, —CH₂C₆H₅, —OCH₃ and —CH₂OCH₃.

By a secondary carbon group is meant the group

wherein the bond represented by the solid line is to a ring atom of an aryl or substituted aryl to which the secondary carbon group is attached, and both free bonds represented by the dashed lines are to an atom or atoms other than hydrogen. These atoms or groups may be the same or different. In other words the free valences represented by the dashed lines may be hydrocarbyl, substituted hydrocarbyl or inert functional groups. Examples of secondary carbon groups include —CH(CH₃)₂, —CHCl₂, —CH(C₆H₅)₂, cyclohexyl, —CH(CH₃)OCH₃, and —CH=CCH₃.

By a "tertiary carbon group" is meant a group of the formula

wherein the bond represented by the solid line is to a ring atom of an aryl or substituted aryl to which the tertiary carbon group is attached, and the three free bonds represented by the dashed lines are to an atom or atoms other than hydrogen. In other words, the bonds represented by the dashed lines are to hydrocarbyl, substituted hydrocarbyl or inert functional groups. Examples of tertiary carbon groups include —C(CH₃)₃, —C(C₆H₅)₃, —CCl₃, —CF₃, —C(CH₃)₂OCH₃, —C≡CH, —C(CH₃)₂CH=CH₂, aryl and substituted aryl such as phenyl and 1-adamantyl.

By "aryl" is meant a monovalent aromatic group in which the free valence is to the carbon atom of an aromatic ring. An aryl may have one or more aromatic rings which may be fused, connected by single bonds or other groups.

By "substituted aryl" is meant a monovalent aromatic group substituted as set forth in the above definition of "substituted hydrocarbyl". Similar to an aryl, a substituted aryl may have one or more aromatic rings which may be fused, connected by single bonds or other groups; however, when the substituted aryl has a heteroaromatic ring, the free valence in the substituted aryl group can be to a heteroatom (such as nitrogen) of the heteroaromatic ring instead of a carbon.

For ligand (I), preferred formulas and compounds (and for their Fe complexes also) are found in previously incorporated U.S. Pat. No. 6,103,946, and preferred groupings and compounds in this application are also preferred herein.

More specifically, the preferred oligomerization catalyst is an Fe complex (Fe[II] or Fe[III]) of a ligand of the general formula (I), wherein:

$R^1$, $R^2$ and $R^3$ are each independently hydrogen, hydrocarbyl, substituted hydrocarbyl or an inert functional group, provided that any two of $R^1$, $R^2$ and $R^3$ vicinal to one another taken together may form a ring;

$R^4$ and $R^5$ are each independently hydrogen, hydrocarbyl, substituted hydrocarbyl or an inert functional group;

$R^6$ and $R^7$ are each independently an aryl or substituted aryl having a first ring atom bound to the imino nitrogen, provided that:

in $R^6$, a second ring atom adjacent to said first ring atom is bound to a halogen, a primary carbon group, a secondary carbon group or a tertiary carbon group; and further provided that in $R^6$, when said second ring atom is bound to a halogen or a primary carbon group, none, one or two of the other ring atoms in $R^6$ and $R^7$ adjacent to said first ring atom are bound to a halogen or a primary carbon group, with the remainder of the ring atoms adjacent to said first ring atom being bound to a hydrogen atom; or in $R^6$, when said second ring atom is bound to a secondary carbon group, none, one or two of the other ring atoms in $R^6$ and $R^7$ adjacent to said first ring atom are bound to a halogen, a primary carbon group or a secondary carbon group, with the remainder of the ring atoms adjacent to said first ring atom being bound to a hydrogen atom; or in $R^6$, when said second ring atom is bound to a tertiary carbon group, none or one of the other ring atoms in $R^6$ and $R^7$ adjacent to said first ring atom are bound to a tertiary carbon group, with the remainder of the ring atoms adjacent to said first ring atom being bound to a hydrogen atom.

By a "first ring atom in $R^6$ and $R^7$ bound to an imino nitrogen atom" is meant the ring atom in these groups bound to an imino nitrogen shown in (I), for example

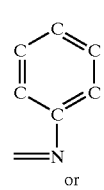

(III)

or

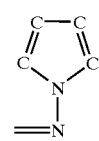

(IV)

the atoms shown in the 1-position in the rings in (III) and (IV) are the first ring atoms bound to an imino carbon atom (other groups which may be substituted on the aryl groups are not shown). Ring atoms adjacent to the first ring atoms are shown, for example, in (V) and (VI), where the open valencies to these adjacent atoms are shown by dashed lines (the 2,6-positions in (V) and the 2,5-positions in (VI)).

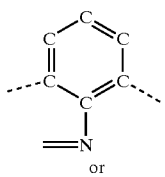

(V)

or

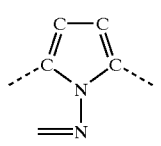

(VI)

Particularly preferred is a ligand of the formula (II):

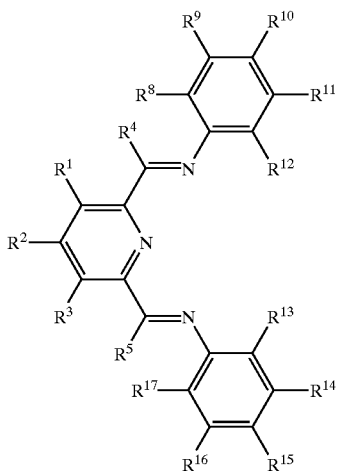

(II)

wherein:
each of $R^1$, $R^2$, $R^3$, $R^4$, $R^5$, $R^9$, $R^{10}$, $R^{11}$, $R^{14}$, $R^{15}$ and $R^{16}$ is independently selected from the group consisting of hydrogen, hydrocarbyl, substituted hydrocarbyl and an inert functional group; and $R^8$ is halogen, a primary carbon group, a secondary carbon group or a tertiary carbon group;

provided that:
when $R^8$ is halogen or a primary carbon group none, one or two of $R^{12}$, $R^{13}$ and $R^{17}$ are independently a primary carbon group, an inert functional group or a trihalo tertiary carbon group, and the remainder of $R^{12}$, $R^{13}$ and $R^{17}$ are hydrogen;

when $R^8$ is a secondary carbon group, none or one of $R^{12}$, $R^{13}$ and $R^{17}$ is a primary carbon group, a secondary carbon group, a trihalo tertiary carbon group or an inert functional group, and the remainder of $R^{12}$, $R^{13}$ and $R^{17}$ are hydrogen;

when $R^8$ is a tertiary carbon group all of $R^{12}$, $R^{13}$ and $R^{17}$ are hydrogen;

any two of $R^1$, $R^2$ and $R^3$ vicinal to one another, taken together may form a ring; and any two of $R^8$, $R^9$, $R^{10}$, $R^{11}$, $R_{12}$, $R^{13}$, $R^{14}$, $R^{15}$, $R^{16}$ and $R^{17}$ vicinal to one another, taken together may form a ring.

In one preferred embodiment of ligand (II), $R^4$ and $R^5$ are methyl or hydrogen; and/or $R^1$, $R^2$, and $R^3$ are all hydrogen; and/or $R^9$, $R^{10}$, $R^{11}$, $R^{14}$, $R^{15}$ and $R^{16}$ are all hydrogen; and/or $R^{17}$ is selected from the group consisting of methyl, ethyl, propyl isopropyl, halo and trihalomethyl; and/or $R^{12}$ is selected from the group consisting of hydrogen, methyl, ethyl, propyl, isopropyl, halo and trihalomethyl. In certain more preferred embodiments, both $R^{12}$ and $R^{17}$ are methyl or ethyl. In all such cases, $R^8$ is a primary carbon group, and $R^{13}$ is hydrogen.

In specific preferred embodiments of ligand (II):
$R^4$ and $R^5$ are methyl; $R^9$, $R^{10}$, $R^{11}$, $R^{13}$, $R^{14}$, $R^{15}$ and $R^{16}$ are all hydrogen; $R^{12}$ is hydrogen or methyl; $R^{17}$ is methyl; and $R^8$ is a primary carbon group; or $R^4$ and $R^5$ are methyl; $R^9$, $R^{10}$, $R^{11}$, $R^{13}$, $R^{14}$, $R^{15}$ and $R^{16}$ are all hydrogen; $R^{12}$ is hydrogen or ethyl; $R^{17}$ is ethyl; and $R^8$ is a primary carbon group; or $R^4$ and $R^5$ are methyl; $R^9$, $R^{10}$, $R^{11}$, $R^{13}$, $R^{14}$, $R^{15}$ and $R^{16}$ are all hydrogen; $R^{12}$ is hydrogen or isopropyl; $R^{17}$ is isopropyl; and $R^8$ is a primary carbon group; or $R^4$ and $R^5$ are methyl; $R^9$, $R^{10}$, $R^{11}$, $R^{13}$, $R^{14}$, $R^{15}$ and $R^{16}$ are all hydrogen; $R^{12}$ is hydrogen or n-propyl; $R^{17}$ is n-propyl; and $R^8$ is a primary carbon group; or $R^4$ and $R^5$ are methyl; $R^9$, $R^{10}$, $R^{11}$, $R^{13}$, $R^{14}$, $R^{15}$ and $R^{16}$ are all hydrogen; $R^{12}$ is hydrogen or chloro; $R^{17}$ is chloro; and $R^8$ is a primary carbon group; or $R^4$ and $R^5$ are methyl; $R^9$, $R^{10}$, $R^{11}$, $R^{13}$, $R^{14}$, $R^{15}$ and $R^{16}$ are all hydrogen; $R^{12}$ is hydorgen or trifluoromethyl; $R^{17}$ is trifluoromethyl; and $R^8$ is a primary carbon group.

In another preferred embodiment of ligand (II), $R^1$, $R^2$, $R^3$, $R^4$, $R^5$, $R^9$, $R^{10}$, $R^{11}$, $R^{14}$, $R^{15}$ and $R^{16}$ are as just defined, and if $R^8$ is a primary carbon group, $R^{12}$ and $R^{17}$ are hydrogen, and $R^{13}$ is a primary carbon group; or if $R^8$ is a secondary carbon group, $R^{12}$ and $R^{17}$ are hydrogen, and $R^{13}$ is a primary carbon group or a secondary carbon group.

Also preferred is when $R^8$ is a primary carbon group, preferably selected from methyl, ethyl, propyls and butyls.

Previously incorporated U.S. Pat. Nos. 5,955,555, 6,103, 946 and WO98/30612, as well as WO99/50273 (equivalent to U.S. patent application Ser. No. 09/277910, now U.S. Pat. No. 6,232,259, filed Mar. 29, 1999) (also incorporated by reference herein for all purposes as if fully set forth), describe synthesis of ligand (I) and its Fe complexes, and reference may be had thereto for further details.

There are many different ways of preparing active oligomerization catalysts from ligand (I) or its Fe complexes many of which are described in previously incorporated U.S. Pat. Nos. 5,955,555, 6,103,946 and WO98/30612, as well as WO99/50273 (equivalent to U.S. patent application Ser. No. 09/277910, now U.S. Pat. No. 6,232,259, filed Mar. 29, 1999), and those so described are applicable herein.

"Pure" Fe complexes may be exemplified by the formula (I)FeX$_n$, wherein each X is an anion, n is 1, 2 or 3 so that the total number of negative charges on the X groups is equal to the oxidation state of the Fe in the pure Fe complex. Preferably, each X is a monovalent anion, more preferably selected from the group consisting of a halide and a nitrile, and especially a halide such as chloride or bromide.

These pure Fe complexes may in and of themselves be active oligomerization catalysts, or they may be activated (or made more active) preferably by preparation in situ by contact with a catalyst activator in a variety of methods. Generally, it has been found that the most active catalysts are those that have been contacted with a catalyst activator.

In general, details for the preparation of oligomers (sometimes referred to as α-olefins) from ethylene using the oligomerization catalysts herein can be found in previously incorporated U.S. Pat. No. 6,103,946, as well as B. L. Small, et. al., *J. Am. Chem. Soc.*, vol. 120, p. 7143–7144 (1998) (also incorporated by reference herein for all purposes as if fully set forth).

Ethylene may be oligomerized by contacting a first compound W, which is a neutral Lewis acid capable of abstracting $X^-$ to form $WX^-$, with an iron halide complex of ligand (I) [or other $X^-$ complex of (I)], provided that the anion formed is a weakly coordinating anion; or a cationic Lewis or Bronsted acid whose counterion is a weakly coordinating anion.

In those instances in which the Fe complex of (I) does not contain an alkyl, hydride, or other group which may be displaced by ethylene already bonded to the metal (i.e., X is not alkyl or hydride), a neutral Lewis acid or a cationic Lewis or Bronsted acid may also alkylate or add a hydride to the metal, i.e., causes an alkyl group or hydride to become bonded to the metal atom, or a separate compound is added to add the alkyl or hydride group.

A preferred neutral Lewis acid, which can alkylate the metal, is a selected alkyl aluminum compound, such as $R^{20}{}_3Al$, $R^{20}{}_3AlCl$, $R^{20}AlCl_2$ and "$R^{20}AlO$" (alkylaluminoxanes), wherein $R^{20}$ is alkyl containing 1 to 25 carbon atoms, preferably 1 to 4 carbon atoms. Suitable alkyl aluminum compounds include methylaluminoxane (which is an oligomer with the general formula $[MeAlO]_n$), $(C_2H_5)_2AlCl$, $(C_2H_5)AlCl_2$ and $[(CH_3)_2CHCH_2]_3Al$. Metal hydrides such as $NaBH_4$ may be used to bond hydride groups to the Fe.

Preferably the oligomer produced by the oligomerization catalyst is a series of compounds of the formula $H_2C=CHR^{28}$, wherein $R^{28}$ is n-alkyl containing an even number of carbon atoms. It is preferred that the series of α-olefins comprises individual α-olefins in which $R^{18}$ contains 2, 4, 6, 8, 10, 12, 14, 16 and optionally higher carbon atoms. Normally, the product of the oligomerization will be a mixture of oligomers of the above formula, preferably possessing a number average molecular weight of about 600 or less, more preferably about 400 or less. Other olefins may optionally be added to the process at any point, so that they also copolymerize into the polyolefin ultimately formed.

If the olefins is made first in series with the copolymerization reaction and thus may be sampled, the olefin series being used may be analyzed, as by gas chromatography, to see if any of the above compositional limits on the olefin series are being met. If the olefin series is produced in situ simultaneously with the copolymerization reaction, it may not be possible to obtain a representative sample of the olefin series. Generally the olefin series will be produced in situ by an ethylene oligomerization catalyst which forms the requisite olefins from ethylene, and is active in the absence of the copolymerization catalyst. In this instance an oligomerization may be run in the absence of the copolymerization catalyst to produce only the series of olefins, under conditions which reasonably mimic the combined oligomerization/copolymerization. The series of olefins thus obtained is then analyzed (as by gas chromatography) to determine if it meets appropriate limitations. Typical analyses of such series of olefins may be found in previously incorporated U.S. Pat. No. 6,103,946. It is assumed herein that the incorporation of α-olefins into a branched polyolefin is in proportion to the relative amounts in which they are present in the polymerization process. This may not be totally correct in the event, for example, that a volatile olefin such as 1-butene is partially "lost" to the polymerization reaction.

Oftentimes when such a series of olefins is made from ethylene a measure of the molecular weights of the olefins obtained is factor K from the Schulz-Flory theory (see for instance B. Elvers, et al., Ed. *Ullmann's Encyclopedia of Industrial Chemistry*, Vol. A13, VCH Verlagsgesellschaft mbH, Weinheim, 1989, p. 243–247 and 275–276. This is defined as:

$$K = n(C_{n+2} \text{ olefin})/n(C_n \text{ olefin})$$

wherein $n(C_n$ olefin) is the number of moles of olefin containing n carbon atoms, and $n(C_{n+2}$ olefin) is the number of moles of olefin containing n+2 carbon atoms, or in other words the next higher oligomer of $C_n$ olefin. From this can be determined the weight (mass) fractions of the various olefins in the resulting oligomeric reaction product mixture. The K factor is preferred to be in the range of about 0.55 to about 0.90, more preferably 0.65 to about 0.80. The K factor may also be varied by changing oligomerization conditions and/or the oligomerization catalyst, see for instance previously incorporated U.S. Pat. No. 6,103,946. By analyzing the branching pattern of the polymer produced one can roughly back calculate the K factor for the oligomerization to α-olefin, although there are possible errors (see below).

The copolymerization catalyst is a catalyst chemically different from the oligomerization catalyst, and which is capable of copolymerizing ethylene and various α-olefins, such as any one or combination of a number of well-known Ziegler-Natta-type or metallocene-type catalysts. Other suitable types of copolymerization catalysts include transition metal complexes of amidimidates and certain iron or cobalt complexes of (I).

The synthesis of the branched copolymers in accordance with the present invention herein can produce unique polymers because of the nature of the two catalysts. In preferred embodiments (discussed below) the oligomerization and copolymerization are performed simultaneously, and/or the oligomerization and copolymerization occur at comparable rates, to prepare various unique copolymers.

In one preferred form the process is carried out in the gas phase, especially when crystalline polymers are desired. It is believed that in many cases in gas phase polymerization when both catalysts are present in the same particle on which polymerization is taking place (for example originally a supported catalyst), the α-olefin is especially efficiently used (polymerized into the resulting polymer). The process may also be carried out in liquid slurry or solution, particularly where amophous or less crystalline copolymers are desired.

As just indicated, the process in accordance with the present invention can produce novel polyethylenes. By "polyethylene" in this instance is meant a polymer produced in a polymerization in which ethylene is the source of at least about 50 mole percent, more preferably at least about 80 mole percent and more preferably at least about 90 mole percent of the repeat units in the polymer. However it is understood that the polymer produced is not made by the direct polymerization of ethylene alone, but by the copolymerization of ethylene and even α-olefins which are produced in situ, and with the odd α-olefin(s) containing (one or more) odd numbers of carbon atoms. The polymer produced usually contains —$R^{18}$ branches present, in other words a polymer containing branches having odd numbers of carbon atoms. The amount of these odd number branches will be related to the amount of odd α-olefin in the polymerization mixture.

In addition, the polymer produced will contain branches of the formula (excluding end groups) —$(CH_2CH_2)_nH$ wherein n is 1 or more. Preferably, the polymer contains 1 to 100, more preferably 1 to 30, of these branches per 1000 methylene atoms. Normally there will be branches with a range of "n" in the polymer. The amount of these branches (as measured by total methyl groups) in the polymer preferably ranges from about 2 to about 200, especially preferably about 5 to about 175, more preferably about 10 to about 150, and especially preferably about 20 to about 150 branches per 1000 methylene groups in the polymer (for the method of measurement and calculation, see U.S. Pat. No. 5,880,241, also incorporated by reference herein). Another preferable range for these branches is about 50 to about 200 methyl groups per 1000 methylene carbon atoms. It is also preferable (either alone or in combination with the other preferable features above) that in these branched polymers there are at least 2 branches each of ethyl and n-hexyl or longer and at least one n-butyl per 1000 methylene groups, more preferably at least 4 branches each of ethyl and n-hexyl or longer and at least 2 n-butyl branches per 1000 methylene groups, and especially preferably at least 10 branches each of ethyl and n-hexyl or longer and at least 5 n-butyl branches per 1000 methylene groups. It is also preferred that there are more ethyl branches than butyl branches in this polyethylene.

In combination with any of the above branching patterns, the polymer preferably also has 1 to 100, more preferably 2 to 20, —$R^{18}$ branches per 1000 methylene groups. Also preferably, the —$R^{18}$ branches are methyl (from propene) and/or propyl (from 1-pentene) branches.

Conditions for such polymerizations, particularly for the oligomerization catalyst, are found in previously incorporated U.S. Pat. No. 6,103,946. Briefly, the temperature at which the polymerization is carried out is about −100° C. to about +200° C. preferably about −20° C. to about +80° C. The polymerization pressure which is used with ethylene is not critical, atmospheric pressure to about 275 MPa, or more, being a suitable range. These polymerizations may be batch, semi-batch or continuous processes, and may be carried out in liquid medium or the gas phase.

In the polymerizations in accordance with the present invention, the resulting polymer preferably has an average degree of polymerization of at least 50, more preferably at least 200, and especially preferably at least 400.

Many types of catalysts are useful as the copolymerization catalyst. For instance so-called Ziegler-Natta and/or metallocene-type catalysts may be used. These types of catalysts are well known in the polyolefin field, see for instance *Angew. Chem., Int. Ed. Engl.,* vol. 34, p. 1143–1170 (1995), EP-A-0416815 and U.S. Pat. No. 5,198,401 for information about metallocene-type catalysts; and J. Boor Jr., *Ziegler-Natta Catalysts and Polymerizations,* Academic Press, New York, 1979 for information about Ziegler-Natta-type catalysts, all of which are hereby included by reference. Many of the useful polymerization conditions for these types of catalysts and the oligomerization catalyst coincide, so conditions for the process are easily accessible. Oftentimes a "co-catalyst" or "activator" is needed for metallocene or Ziegler-Natta-type polymerizations, much as W is sometimes needed for the oligomerization catalyst. In many instances the same compound, such as an alkylaluminum compound, may be used for these purposes for both types of catalysts.

Suitable catalysts for the copolymerization catalyst also include metallocene-type catalysts, as described in U.S. Pat. No. 5,324,800 and EP-A-0129368; particularly advantageous are bridged bis-indenyl metallocenes, for instance as described in U.S. Pat. No. 5,145,819 and EP-A-0485823. Another class of suitable catalysts comprises the well-known constrained geometry catalysts, as described in EP-A-0416815, EP-A-0420436, EP-A-0671404, EP-A-0643066 WO91/04257. Also the class of transition metal complexes described in, for example, WO98/30609, U.S. Pat. Nos. 5,880,241, 5,955,555, 6,060,569 and 5,714,556 can be used. Metallocene catalysts already known for the copolymerization of active nonconjugated dienes are described in U.S. Pat. No. 5,229,478, WO88/04674, WO99/18135 and WO99/01460, and references described therein. All of the aforementioned publications are incorporated by reference herein for all purposes as if fully set forth.

All the catalysts herein may be "heterogenized" (to form a polymerization catalyst component, for instance) by coating or otherwise attaching them to solid supports, such as silica or alumina. Where an active catalyst species is formed by reaction with a compound such as an alkylaluminum compound, a support on which the alkylaluminum compound is first coated or otherwise attached is contacted with the transition metal compounds (or their precursors) to form a catalyst system in which the active polymerization catalysts are "attached" to the solid support. These supported catalysts may be used in polymerizations in organic liquids. They may also be used in so-called gas phase polymerizations in which the olefin(s) being polymerized are added to the polymerization as gases and no liquid supporting phase is present. The transition metal compounds may also be coated onto a support such as a polyolefin (polyethylene, polypropylene, etc.) support, optionally along with other needed catalyst components such as one or more alkylaluminum compounds.

The oligomers made by the oligomerization catalyst and the polymer made by the polymerization catalyst may be made in sequence, i.e., the oligomerization followed by the polymerization, as by using two vessels in series. For example, ethylene can be oligomerized in a first reactor in the presence of the oligomerization catalyst to produce an oligomer mixture, which is then transferred to a second reactor with odd α-olefin (to the extent not already present in the first monomer mixture) and additional ethylene/α-olefin feed (to the extent necessary), and copolymerization catalyst, in the amounts and under polymerization conditions required for the desired end product.

However it is preferred to carry out the entire process in the same vessel(s), i.e., carrying out steps (1) and (2) sequentially or simultaneously. This is possible because in most instances the oligomerzation/polymerization catalysts and conditions are compatible with each other.

One such preferred process is to contact ethylene and the oligomerization catalyst for a period of time sufficient to oligomerize a portion of the ethylene to α-olefins, after which the copolymerization catalyst is added to the vessel. The odd α-olefin, additional ethylene as needed, and other α-olefins as desired, can be added at any stage during the process.

Another preferred process is to add all components to the vessel at the same time—ethylene, odd α-olefin, oligomerization catalyst and copolymerization catalyst—and conduct the oligomerization/copolymerization simultaneously. In this case, the amount of branching due to incorporation of the α-olefins (both odd and even) in the polymer can be controlled by the ratio of oligomerization catalyst to copolymerization catalyst. The higher the proportion of oligomerization catalyst the higher the amount of branching in the resulting copolymer.

In all of these processes, it preferred to use essentially only ethylene and the odd α-olefin as monomers added into the process. Of course, other monomers/oligomers will be generated in situ and incorporated into the final copolymer, but the only monomers required to operate the process and generate the products are ethylene and the odd α-olefin.

A particularly preferred aspect of the process utilizes ethylene and the odd α-olefin as the sole added monomers, with the even α-olefins being incorporated into the final copolymer solely as a result of the in situ oligomerization of ethylene.

In the Examples, all pressures are gauge pressures.

In the Examples PMAO-IP is a form of methylaluminoxane which stays in solution in toluene, and is commercially available. In the Examples all pressures are gauge pressures. In the Examples the following compounds are used:

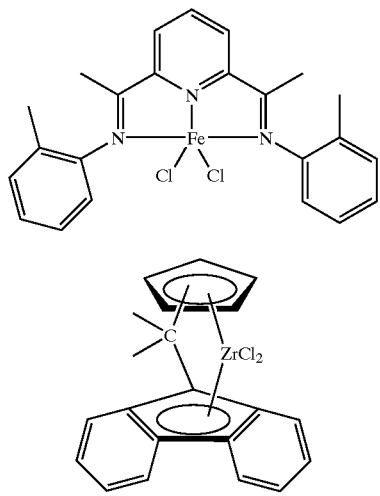

A

B

In the Examples, the following abbreviations are used:
DSC—differential scanning calorimetry
GPC—gel permeation chromatography
MAO—methylaluminoxane
MI—melt index
Mn—number average molecular weight
PE—polyethylene
RT—room temperature
TCE—tetrachloroethane Supported catalyst used in the Examples was made by stirring a mixture of isopropylidene(cyclopentadienyl)(9-fluorenyl)zirconium dichloride (B, 1.0 mg), 109.2 mg (weight of solution) 0.1 wt % A in biphenyl, 0.35 g silica supported methylaluminoxane (18 wt % in Al) and 15 mL toluene. After shaking for 30 min, the solid was filtered, washed with 3×5 mL toluene and dried in vacuo for 1 h. It was then stored in a freezer and was used the next day.

EXAMPLE 1

A 600 mL Parr® autoclave was cleaned and was charged with 150 g of well baked NaCl. It was dried under full vacuum at 120° C. for 2 h. It was then charged with 690 kPa of nitrogen while it was still hot. A hot water bath was prepared by heating it to 85° C. In a drybox, 0.66 mL 13.5 wt % MAO (improved processing) toluene solution was mixed with 4 mL of toluene. It was transferred to a 5 mL syringe. This was brought out of the drybox and the solution was injected to the autoclave under positive nitrogen pressure. The mixture was stirred (600 RPM) under 690 kPa nitrogen for 30 min. Stirring was stopped. In a drybox, 120 mg of freshly made silica supported catalyst was mixed with 4.5 mL cyclohexane. This was transferred to a 5 mL gas tight syringe. It was brought out of the drybox. The mixture was then injected to the autoclave under positive nitrogen pressure. The mixture was then allowed to stir (600 RPM) under 690 kPa nitrogen for 15 min. Stirring was stopped. Nitrogen was released to 14 kPa. The autoclave was evacuated under full vacuum for 15 min, with stirring the last 5 min. It was re-charged with 1.17 MPa nitrogen, then released to 14 kPa twice. The mixture was allowed to stir at 500 RPM. Ethylene was added (350 kPa). It was then pressured with propene up to 690 kPa total (350 kPa propene). Finally the total pressure of the reactor was adjusted to 2.41 MPa by feeding ethylene. The reactor was placed in the 85° C. water bath. The mixture was allowed to stir at 80° C. to 90° C. for 2 h. The autoclave was vented and the polymer isolated. $^1$HNMR(TCE-d$_2$, 120° C.): 65Me/1000CH$_2$. GPC(PE standard, 135° C.): Mw=31,744; Mn=5,464; PD=5.81. The polymer had a melting point of 124° C. (13.0 J/g) based on DSC. MI=6.3. The density was 0.891 g/mL based on IR. $^{13}$C NMR indicated that there were 61.7 Me/1000 CH$_2$, and branching distribution (per 1000 CH$_2$ groups) was: Me=41.3; Et=5.5; pr=0.0; Bu=3.9; Am=0.0; Hex+=11.5.

EXAMPLE 2

A 600 mL Parr® autoclave was cleaned, heated up under vacuum and then allowed to cool under nitrogen. It was then brought into a drybox. In the drybox, to a Hoke® cylinder was added 5 mL toluene and 1.0 mL MAO (13.5 wt % toluene solution). To a 20 mL vial was added 4.0 mg of B and 16 mL toluene. Only 2 mL of this solution was pipet transferred to the 600 mL autoclave. Then 57.2 mg of a 0.1 wt % A in biphenyl (solid) solution (weight of solution) was also added to the autoclave, followed by addition of 250 mL 2,2,4-trimethylpentane and 25 g 1-pentene. The autoclave was sealed. Both the Hoke® cylinder and the autoclave were brought out of the drybox. The autoclave was assembled to a high pressure line. The Hoke® cylinder was then connected to the autoclave. The autoclave was pressured up with nitrogen. The autoclave was heated to 85° C, and nitrogen was released to 21 kPa. It was then pressurized up with 2× to 690 kPa ethylene, venting each time and finally pressurized to 830 kPa ethylene with stirring. The MAO solution was added from the Hoke® cylinder at slightly higher pressure. The ethylene pressure of the reactor was then adjusted to 1.24 MPa. The reaction mixture was allowed to stir at 88° C.–99° C. for 60 min. The heating source was removed. Ethylene was vented to about 210 kPa. The autoclave was back filled with 1.38 MPa nitrogen and was then vented to 210 kPa. This was repeated. The reaction mixture was then cooled to RT. The reaction mixture was slowly poured into 400 mL methanol, followed by addition of 6 mL conc. HCl. After stirring at RT for 25 min, polymer was filtered, washed with methanol six times and dried in vacuo. White polymer (24.87 g) was obtained.

What is claimed is:

1. A process for preparing a branched polyolefin, comprising the steps of: (1) contacting an ethylene oligomerization catalyst and a first monomer component comprising ethylene, under conditions to oligomerize at least a portion of the ethylene to one or more even α-olefins of the general formula $R^{28}CH=CH_2$ wherein $R^{28}$ is alkyl containing an even number of carbon atoms, wherein the ethylene oligomerization catalyst comprises an active Fe complex of a ligand of the formula (I):

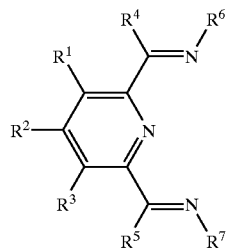
(I)

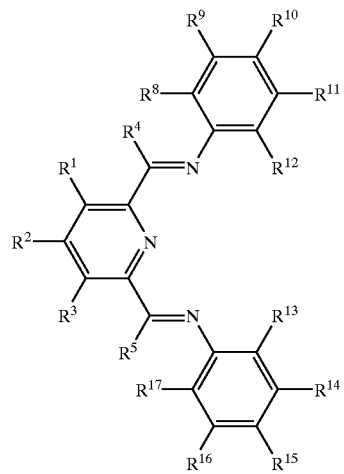
(II)

wherein:
$R^1$, $R^2$, $R^3$, $R^4$ and $R^5$ are each independently hydrogen, hydrocarbyl, substituted hydrocarbyl, or an inert functional group, provided that any two of $R^1$, $R^2$ and $R^3$ vicinal to one another, taken together may form a ring; and $R^6$ and $R^7$ are aryl or substituted aryl; and (2) contacting an active transition metal copolymerization catalyst, with a second monomer component comprising ethylene, at least a portion of the α-olefin from step (1) and an odd α-olefin of the formula $R^{18}CH=CH_2$ wherein $R^{18}$ is alkyl containing an odd number of carbon atoms, under conditions to copolymerize the ethylene, even α-olefin and odd α-olefin to a branched polyolefin.

2. The process as recited in claim 1 wherein the oligomerization catalyst is an Fe complex of a ligand of the general formula (I), wherein:

$R^1$, $R^2$ and $R^3$ are each independently hydrogen, hydrocarbyl, substituted hydrocarbyl or an inert functional group, provided that any two of $R^1$, $R^2$ and $R^3$ vicinal to one another taken together may form a ring;

$R^4$ and $R^5$ are each independently hydrogen, hydrocarbyl, substituted hydrocarbyl or an inert functional group;

$R^6$ and $R^7$ are each independently an aryl or substituted aryl having a first ring atom bound to the imino nitrogen, provided that:
in $R^6$, a second ring atom adjacent to said first ring atom is bound to a halogen, a primary carbon group, a secondary carbon group or a tertiary carbon group; and further provided that in $R^6$, when said second ring atom is bound to a halogen or a primary carbon group, none, one or two of the other ring atoms in $R^6$ and $R^7$ adjacent to said first ring atom are bound to a halogen or a primary carbon group, with the remainder of the ring atoms adjacent to said first ring atom being bound to a hydrogen atom; or in $R^6$, when said second ring atom is bound to a secondary carbon group, none, one or two of the other ring atoms in $R^6$ and $R^7$ adjacent to said first ring atom are bound to a halogen, a primary carbon group or a secondary carbon group, with the remainder of the ring atoms adjacent to said first ring atom being bound to a hydrogen atom; or in $R^6$, when said second ring atom is bound to a tertiary carbon group, none or one of the other ring atoms in $R^6$ and $R^7$ adjacent to said first ring atom are bound to a tertiary carbon group, with the remainder of the ring atoms adjacent to said first ring atom being bound to a hydrogen atom.

3. The process a recited in claim 2 wherein the oligomerization catalyst comprises an active Fe complex of a ligand of the formula (II):

wherein:
each of $R^1$, $R^2$, $R^3$, $R^4$, $R^5$, $R^9$, $R^{10}$, $R^{11}$, $R^{14}$, $R^{15}$ and $R^{16}$ is independently selected from the group consisting of hydrogen, hydrocarbyl, substituted hydrocarbyl and an inert functional group; and $R^8$ is halogen, a primary carbon group, a secondary carbon group or a tertiary carbon group;

provided that:
when $R^8$ is halogen or a primary carbon group none, one or two of $R^{12}$, $R^{13}$ and $R^{17}$ are independently a primary carbon group, an inert functional group or a trihalo tertiary carbon group, and the remainder of $R^{12}$, $R^{13}$ and $R^{17}$ are hydrogen;

when $R^8$ is a secondary carbon group, none or one of $R^{12}$, $R^{13}$ and $R^{17}$ is a primary carbon group, a secondary carbon group, a trihalo tertiary carbon group or an inert functional group, and the remainder of $R^{12}$, $R^{13}$ and $R^{17}$ are hydrogen;

when $R^8$ is a tertiary carbon group all of $R^{12}$, $R^{13}$ and $R^{17}$ are hydrogen;

any two of $R^1$, $R^2$ and $R^3$ vicinal to one another, taken together may form a ring; and any two of $R^8$, $R^9$, $R^{10}$, $R^{11}$, $R^{12}$, $R^{13}$, $R^{14}$, $R^{15}$, $R^{16}$ and $R^{17}$ vicinal to one another, taken together may form a ring.

4. The process as recited in claim 1 wherein the copolymerization catalyst is a metallocene-type catalyst.

5. The process as recited in claim 2 wherein the copolymerization catalyst is a metallocene-type catalyst.

6. The process as recited in claim 1 wherein steps (1) and (2) are conducted sequentially or simultaneously in the same reactor vessel.

7. The process as recited in claim 6 wherein steps (1) and (2) are conducted simultaneously in the same reactor vessel.

8. The process as recited in claim 1 wherein the oligomerization and copolymerization catalysts are supported.

9. The process as recited in claim 8 carried out in the gas phase.

10. The process as recited in claim 7 wherein the oligomerization and copolymerization occur at comparable rates.

11. The process as recited in claim 1, wherein the odd α-olefin is selected from the group consisting of propene and pentene.

12. The process as recited in claim 1 wherein the first monomer component consists essentially of ethylene and optionally an odd α-olefin, and the second monomer component consists essentially of ethylene, at least a portion of the α-olefins from step (1) and the odd α-olefin.

13. The process as recited in claim 5 wherein steps (1) and (2) are conducted simultaneously in the same reactor vessel; the oligomerization and copolymerization catalysts are supported; the process is carried out in the gas phase; the oligomerization and copolymerization occur at comparable rates; the first monomer component consists essentially of ethylene and optionally an odd α-olefin; and the second monomer component consists essentially of ethylene, at least a portion of the α-olefins from step (1) and the odd α-olefin.

* * * * *